United States Patent [19]
Sperl

[11] Patent Number: 6,020,379
[45] Date of Patent: Feb. 1, 2000

[54] POSITION 7 SUBSTITUTED INDENYL-3-ACETIC ACID DERIVATIVES AND AMIDES THEREOF FOR THE TREATMENT OF NEOPLASIA

[75] Inventor: Gerhard Sperl, North Wales, Pa.

[73] Assignee: Cell Pathways, Inc., Horsham, Pa.

[21] Appl. No.: 09/253,555

[22] Filed: Feb. 19, 1999

[51] Int. Cl.[7] .......................... C07C 317/04; A61K 31/19
[52] U.S. Cl. .......................... 514/569; 514/277; 514/562; 562/428
[58] Field of Search .................................. 514/569, 562, 514/277; 562/428

[56] References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,865,840 | 2/1975 | Carson . |
| 3,920,636 | 11/1975 | Takahashi et al. . |
| 3,954,852 | 5/1976 | Shen ........................................ 260/515 |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,076,711 | 2/1978 | Ganguly et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,457,927 | 7/1984 | Biere et al. . |
| 4,460,590 | 7/1984 | Möller . |
| 4,460,591 | 7/1984 | DeGraw et al. . |
| 4,880,810 | 11/1989 | Lowe, III et al. . |
| 4,885,301 | 12/1989 | Coates . |
| 4,923,874 | 5/1990 | McMahon et al. . |
| 4,971,972 | 11/1990 | Doll et al. . |
| 5,073,559 | 12/1991 | Coates . |
| 5,091,431 | 2/1992 | Tulshian et al. . |
| 5,147,875 | 9/1992 | Coates et al. . |
| 5,175,151 | 12/1992 | Afonso et al. . |
| 5,223,501 | 6/1993 | Chakravarty et al. . |
| 5,250,535 | 10/1993 | Verheyden et al. . |
| 5,254,571 | 10/1993 | Coates et al. . |
| 5,358,952 | 10/1994 | Moschel et al. . |
| 5,376,683 | 12/1994 | Klar et al. . |
| 5,393,755 | 2/1995 | Neustadt et al. . |
| 5,439,895 | 8/1995 | Lee et al. . |
| 5,488,055 | 1/1996 | Kumar et al. . |
| 5,614,530 | 3/1997 | Kumar et al. . |
| 5,614,627 | 3/1997 | Takase et al. . |
| 5,696,159 | 12/1997 | Gross et al. . |
| 5,728,563 | 3/1998 | Mie . |
| 5,756,818 | 5/1998 | Buchmann et al. . |
| 5,784,440 | 7/1998 | Pamukcu et al. . |
| 5,852,035 | 12/1998 | Pamukcu et al. . |
| 5,858,694 | 1/1999 | Piazza et al. . |
| 5,874,440 | 7/1998 | Pamukcu et al. . |

FOREIGN PATENT DOCUMENTS

| | | |
|---|---|---|
| 0 330 004 A1 | 6/1989 | European Pat. Off. . |
| 0 347 146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 0 722937 A1 | 7/1996 | European Pat. Off. . |
| 0 743304 A1 | 10/1996 | European Pat. Off. . |
| 274218 | 12/1989 | Germany . |
| 56-53659 | 5/1981 | Japan . |
| 57-167974 | 10/1982 | Japan . |
| 8-311035 | 11/1996 | Japan . |
| 807826 | 1/1959 | United Kingdom . |
| 3038166 | of 1981 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 94/19351 | 9/1994 | WIPO . |
| WO 94/29277 | 12/1994 | WIPO . |
| WO 95 18969 | 7/1995 | WIPO . |
| WO 95/26743 | 10/1995 | WIPO . |
| WO 97/03070 | 1/1997 | WIPO . |
| WO 97/03985 | 2/1997 | WIPO . |
| WO 97/24334 | 7/1997 | WIPO . |
| WO 98/14448 | 4/1998 | WIPO . |
| WO 98/15530 | 4/1998 | WIPO . |
| WO 98/16224 | 4/1998 | WIPO . |
| WO 98/16521 | 4/1998 | WIPO . |
| WO 98/17668 | 4/1998 | WIPO . |
| WO 98/08848 | 5/1998 | WIPO . |
| WO 98/23597 | 6/1998 | WIPO . |
| WO 98/38168 | 9/1998 | WIPO . |
| WO 96/32379 | 10/1998 | WIPO . |

OTHER PUBLICATIONS

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

(List continued on next page.)

*Primary Examiner*—Robert Gerstl
*Attorney, Agent, or Firm*—Robert W. Stevenson

[57] ABSTRACT

In position 7 substituted indenyl-3-acetic acid derivatives and pharmaceutically acceptable salts and amides thereof have anti-neoplastic activity.

3 Claims, No Drawings

OTHER PUBLICATIONS

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., "Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–phridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors of the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3'–5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1994, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak ikn guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324 (1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., "Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Ho–Sam Ahn et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

J.A. Mitchell et al., Selectivity of nonsteroidal antiinflammatory drugs as inhibitors of constitutive and inducible cyclooxygenase; Proc. Natl. Acad. Sci. USA, vol. 90, Dec. 1994, pp. 11693–11697.

J.D. Gaffen et al.: Increased killing of malignant cells by giving indomethacin with methotrexate, p. 30; col. 1; XP002084860Chemical Abstract, vol. 106, No. 11, Mar. 16, 1987, abstract No. 78377, J.D.

Tsou, K–C. et al. 5'–Nucleotide Phosphodiesterase Isozyme–V as a Marker for Liver Metastases in Breast Cancer Patients, Cancer 54:1788–1793, 1984.

Epstein P M et al.; Dep. Pharmacol., Univ. Tex. Med. Sch., M.D. Anderson Hosp., Houston, Tex. 88030, USA Biosis 78:140912, "Increased Cyclic Nucleotide Phospho Di Esterase Activity Associated With Proliferation and Cancer in Human and Murine Lymphoid Cells.

Christian Schudt et al., "Phosphodiesterase Inhibitors" The Handbook of Immunopharmacology, Academic Press, 1996, pp. 65–134.

POSITION 7 SUBSTITUTED INDENYL-3-ACETIC ACID DERIVATIVES AND AMIDES THEREOF FOR THE TREATMENT OF NEOPLASIA

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical dysplasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programaned cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which cause gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans (see Piaza et al. Gastroenterology Vol. 112, A629, 1997). Thus, the severe side effects due to induction of apoptosis in normal cells by conventional chemotherapeutics are avoided by these novel therapeutics (see, Piazza et al. Cancer Research Vol. 57, pp. 2452–2459, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents compounds that inhibit the growth of neoplastic cells, for treating patients with neoplastic lesions. This invention also involves methods for inducing such specific inhibition of neoplastic cells by exposing such cells to a pharmacologically effective amount of those compounds described below to a patient in need of such treatment. Such compositions are effective in modulating the growth of neoplasms.

DETAILED DESCRIPTION OF THE PREFERRED EMBODIMENTS

This invention comprises compounds of the Formula:

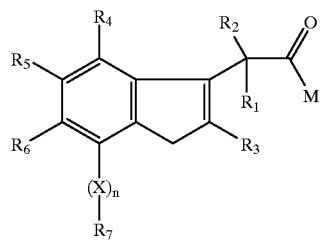

wherein $R_1$ and $R_2$ are independently selected in each instance from the group consisting of hydrogen, alkyl, amino, and —C=O;

$R_3$ is selected from the group consisting of hydrogen and lower alkyl;

M is selected from the group consisting of hydroxy, OMe, or NR' R";

Me is a cation;

R' is selected from the group consisting of hydrogen, loweralkyl, dialkylaminoalkyl, hydroxyalkyl, aminoalkyl, alkoxy, alkenyl, alkynyl, polyhydroxyalkyl, benzyl, phenyl, indane, phenylalkyl, benzylalkyl, pyridinylalkyl, pyrrolylalkyl, pyrrolidinylalkyl, pyrazolylalkyl, pyrazolidinylalkyl, imidazolylalkyl, imidazolidinylalkyl, piperidinylalkyl, pyrazinylalkyl, piperazinylalkyl, pyrimidinylalkyl, morpholinylalkyl, tetrazolylalkyl, triazinylalkyl, furfurylalkyl, thiophenylalkyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl;

R" is selected from the group consisting of hydrogen, lower alkyl, cyanoalkyl, haloalkyl, aminoalkyl, dialkylamino alkyl, alkanoylalkylester and pyridinyl X is selected from the group consisting of lower alkyl, lower alkenyl, lower alkynyl, $S(O)_m$, —C=O, —C(O)O—, —O(O)C—, —$S(O)_2NR$—, —$NRS(O)_2$—, —C(O)NR—, —NRC(O)—, —$CH_2O$, $OCH_2$—, —O—, —NR—, —$S(O)_2O$—, and —$OS(O)_2$—;

R is selected from the group consisting of hydrogen, lower alkyl, and lower alkanoyl;

n is 0 or 1; m is 0,1, or 2;

$R_4$, $R_5$, and R6 are independently selected in each instance from the group consisting of hydrogen, halogen, alkyl, alkanoyloxy, alkoxy, acylamino, alkylamino, dialkylamino, dialkylaminoalkyl, sulfamyl, alkylthio, hydroxy, hydroxyalkyl, alkenyl, alkenyloxy, alkylsulfonyl, alkylsulfinyl, carboxyl, carbalkoxy, carbamido, and cyano;

$R_7$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfilryl, and thiophenyl, wherein the substitutents on the $R_7$ ring are one to three substituents selected from the group consisting of halogen, lower alkyl, lower alkoxy, amino, lower alkylamino, hydroxy, nitro, cyano, dilower alkylamino, lower alkyl mercapto, lower alkyl sulfinyl, lower alkyl sulfonyl, acylamino, hydroxyalkyl, carboxyl, carbalkoxy, and carbamido; and pharmaceutically acceptable salts thereof.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I, wherein $R_1$, $R_2$, $R_3$, $R_4$, $R_5$, $R_6$, $R_7$, M etc are defined as above.

In still another form, this invention is a method of inducing apoptosis in human cells by exposing those cells to an effective amount of compounds of Formula I, wherein $R_1$ through $R_7$, M etc. are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ through $R_7$ etc. are defined as above. The regulation of apoptosis is believed to play an important role in diseases associated with abnormalities of cellular growth patterns such as benign prostatic hyperplasia, neurodegenerative diseases such as Parkinson's disease, autoinimune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "lower alkyl mercapto" refers to a sulfide group that is substituted with a lower alkyl group; and the term "lower alkyl sulfonyl" refers to a sulfone group that is substituted with a lower alkyl group.

The term "hydroxyalkyl" refers to a lower alkyl group substituted with 1–3 hydroxy groups.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional crystallization of diastereomeric salts and the like.

Compounds of Formula I also can exist as geometrical isomers (Z and E); the Z isomer is preferred.

Compounds of this invention may be formulated into pharmaceutical compositions together with pharmaceutically acceptable carriers for oral administration in solid or liquid form, or for rectal, intravenous, or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfaming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel. Pharmaceutically acceptable carriers for intraveneous administration include solutions containing pharmaceutically acceptable salts or sugars.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day. It is believed that the dosage of compounds of this invention in humans would range from 6–600 mg in the average adult.

The pharmaceutical compositions of this invention are preferably packaged in a container (e.g., a box or bottle, or both) with suitable printed material (e.g., a package insert) containing indications, directions for use, etc.

There is one general scheme for producing compounds useful in this invention.

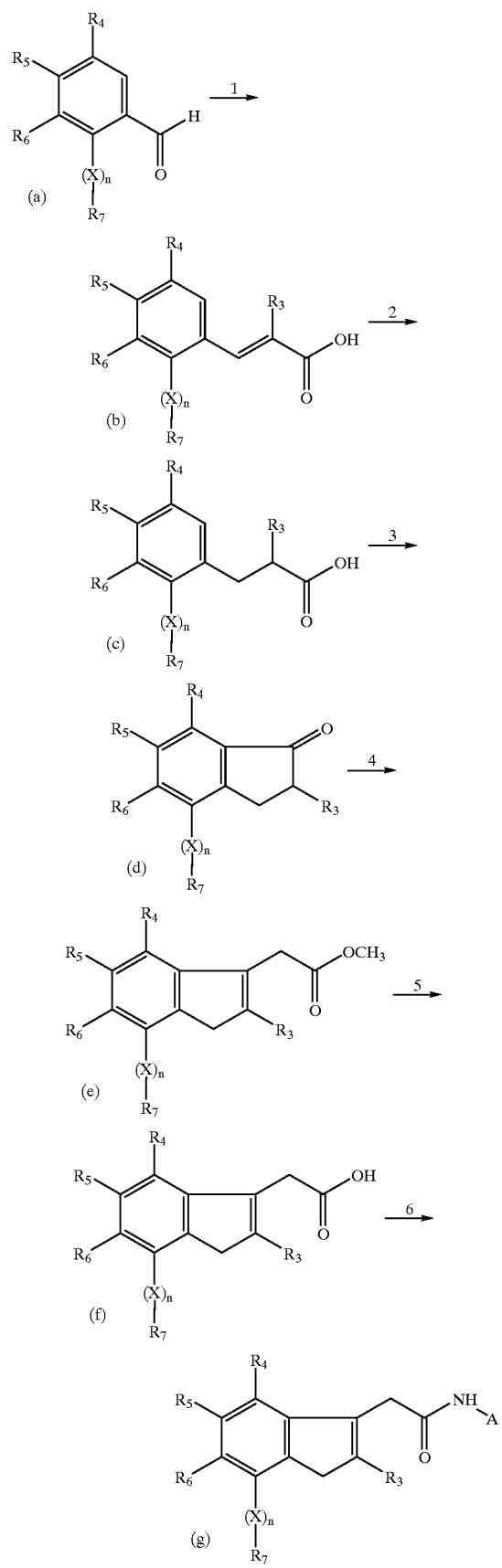

In general, an aldehyde (a) is heated with propionic anhydride and sodium propionate to give a cinnamic acid derivative (b) (reaction 1). The hydrogenation of the cinnamic acid (b) is performed with hydrogen on $PtO_2$ in ethyl acetate under 40 p.s.i. (reaction 2). The resulting propionic acid (c) is allowed to react with polyphosphoric acid to obtain the indanone (d) (reaction 3), which subsequently undergoes a Reformatsky reaction by being refluxed with zinc dust, methyl bromoacetate and iodine in an inert solvent such as benzene. Refluxing with phosphorus pentoxide yields the indenylmethyl acetate (e) (reaction 4). The ester (e) is hydrolized with sodium hydroxide in alcohol (reaction 5). Acidic work up gives the acetic acid (f), which is transformed to the acid chloride through reaction with oxalyl chloride and then is allowed to react with an amine to give the amide (g) (reaction 6).

The reagents and conditions for the general scheme are as follows:
1. Propionic anhydride, sodium propionate, 135° C.
2. Hydrogenation: $H_2/PtO_2$, ethyl acetate, 42 p.s.i.
3. Polyphosphoric acid or: a) oxalyl chloride
   b) $AlCl_3$
4. a) Reformatsky: Zn, alkylbromoacetate, $I_2$, inert solvent, reflux
   b) $P_2O_5$, reflux
5. a) hydrolysis: NaOH, alcohol, reflux
   b) HCl
6. a) oxalyl chloride
   b) amine or: coupling reagent (carbodiimide), amine There are several schemes to obtain the starting compound (a) for the general scheme above.

If n is 0, scheme I below is used to synthesize the aldehyde (a)

Scheme I (n=0)

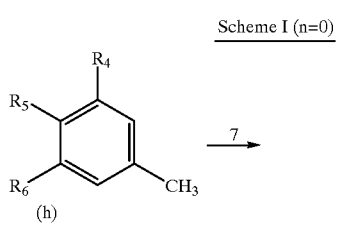
(h)

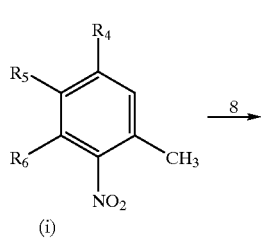
(i)

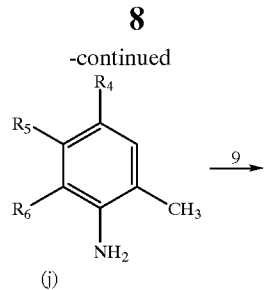
(j)

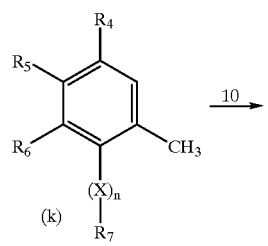
(k)

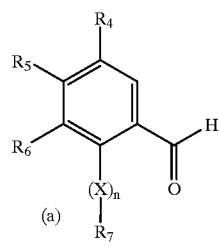
(a)

The toluene derivative (h) is charged with concentrated sulfuric acid and potassium nitrate to obtain the 2-nitrotoluene derivative (i) (reaction 7), which is subsequently reduced (reaction 8) with hydrogen over Raney-nickel to the amine (j). In a Sandmeyer reaction (reaction 9) with amylnitrate and the halogenide ($R_7$-Hal) in the presence of copper, the toluene derivative (k) is obtained. The reaction with chromium(VI)oxide in acetic acid leads to the aldehyde (a).

The reagents and conditions of scheme I are as follows:

7. conc. $H_2SO_4$, $KNO_3$
8. $H_2$/Raney-nickel
9. Sandmeyer reaction: $Cu^0$, amylnitrate, $R_7$-Hal
10. $CrO_3$, acetic acid If X is ethylene or ethyl, the following scheme II is used to obtain the starting aldehyde compound (a).

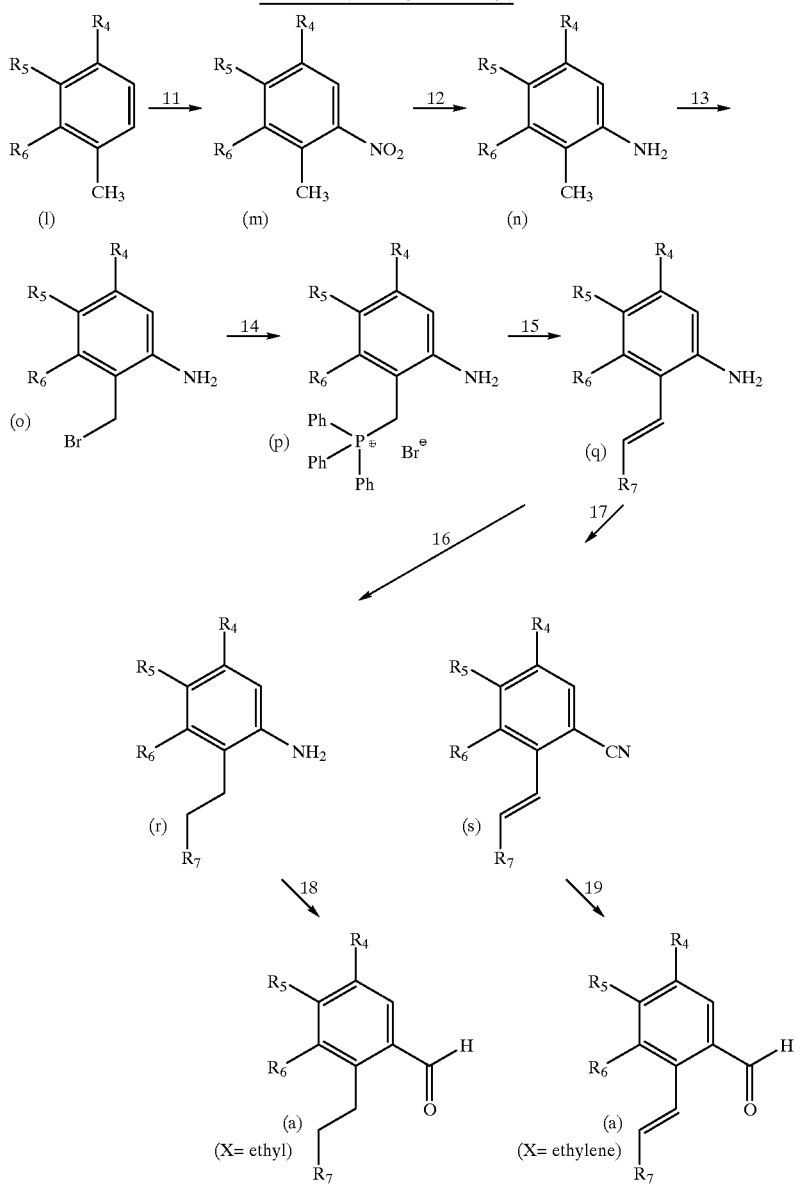

Scheme II (X = ethylene or ethyl)

The toluene derivative (1) is charged with concentrated sulfuric acid and potassium nitrate (reaction 11) to obtain the 2-nitro toluene (m), which subsequently is reduced (reaction 12) with hydrogen on palladium/charcoal to the amine (n). The methyl group of the amine (n) is brominated with bromine under illumination (reaction 13). The brominated aniline (o) is charged (reaction 14) with triphenylphosphine in dimethylformamide to give the phosphonium salt (p), which undergoes a Wittig reaction (reaction 15) with n-butyl-lithium and the aldehyde $R_7$—C(O)H. The ethylene-substituted aniline (q) is reduced with hydrogen over palladium-charcoal to the ethyl-substituted aniline (r) (reaction 16), which is further allowed to react with $NaNO_2$ and $H_2SO_4$, followed by copper cyanide, and is then heated with formic acid over Raney-nickel to obtain the aldehyde (a) (reaction 18). The ethylene-substituted aniline (q) can also be charged with $NaNO_2$ and $H_2SO_4$, followed by copper cyanide (reaction 17), which is then heated with formic acid over Raney-nickel (reaction 19) to give the ethylene-substituted aldehyde (a).

The reagents and conditions for scheme II are as follows:
11. concentrated $H_2SO_4$, $KNO_3$
12. $H_2$, Pd/C
13. $Br_2$, hv
14. $PhP_3$, DMF
15. Wittig reaction: n-BuLi, aldehyde
16. $H_2$, Pd/C
17. a) $NaNO_2$, $H_2SO_4$
    b) CuCN
18. a) $NaNO_2$, $H_2SO_4$
    b) CuCN
    c) HCOOH, Raney-nickel, temp.
19. HCOOH, Raney-nickel, temp.

If X is sulfur, sulfoxide or sulfone, the following scheme III is applied to obtain the aldehyde (a).

Scheme III (X = S, SO, SO$_2$)

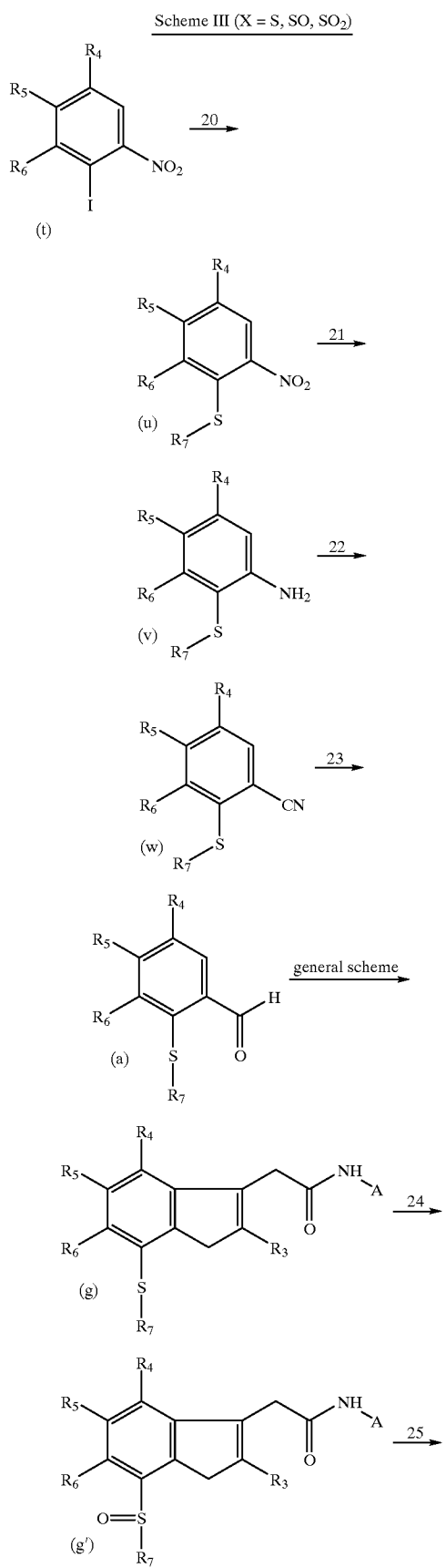

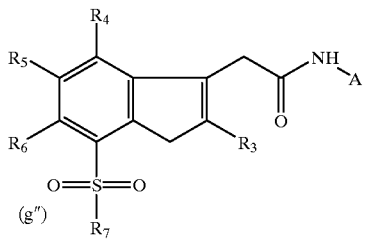

The substituted iodo-nitrobenzene (t) is charged with sodium hydride and the mercaptan R$_7$—SH in dimethylformamide (reaction 20) to obtain the mercapto-substituted compound (u). The nitrogroup of compound (u) is reduced with hydrogen on palladium-charcoal to give the aniline derivative (v) (reaction 21), which is then charged with NaNO$_2$ and sulfuric acid, followed by copper cyanide, to yield the nitrile (w) (reaction 22). The nitrile (w) is heated with formic acid in the presence of Raney-nickel (reaction 23) to give the aldehyde (a).

To obtain the sulfoxide and sulfone derivative, the general scheme is followed with the mercapto-substituted aldehyde (a) to obtain the mercapto-substituted amide (g). Oxidation of the mercapto-group with hydrogen peroxide (reaction 24) gives the sulfoxide-substituted amide (g') and further reaction with oxone® leads to the sulfone derivative (g") (reaction 25).

The reagents and conditions for scheme III are as follows:

20. a) SH-R$_7$, DMF
    b) NaH
21. H$_2$, Pd/C
22. a) NaNO$_2$, H$_2$SO$_4$
    b) CuCN
23. HCOOH, Raney-Ni, temp.
24. Oxidation: H$_2$O$_2$ (30%)
25. Oxoneg®

If X is carbonyl, the following scheme IV is used to obtain the aldehyde (a).

Scheme IV (X = CO)

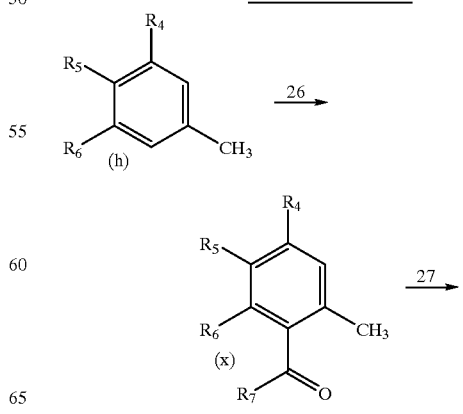

-continued

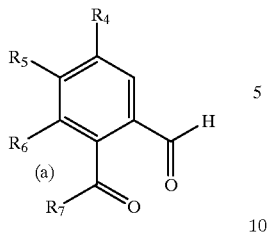

The substituted toluene (h) is reflexed with the acid halogenide $R_7$—C(O)-Hal and trifluoromethane sulfonic acid (reaction 26) to yield the keto-derivative (x). Reaction with $CrO_3$ in acetic acid (reaction 27) yields the aldehyde (a).

The reagents and conditions for scheme IV are as follows.

26. $R_7$—C(O)-Hal, trifluoromethane sulfonic acid, reflux
27. $CrO_3$, AcOH

If X is a secondary amino group, the following scheme V is used.

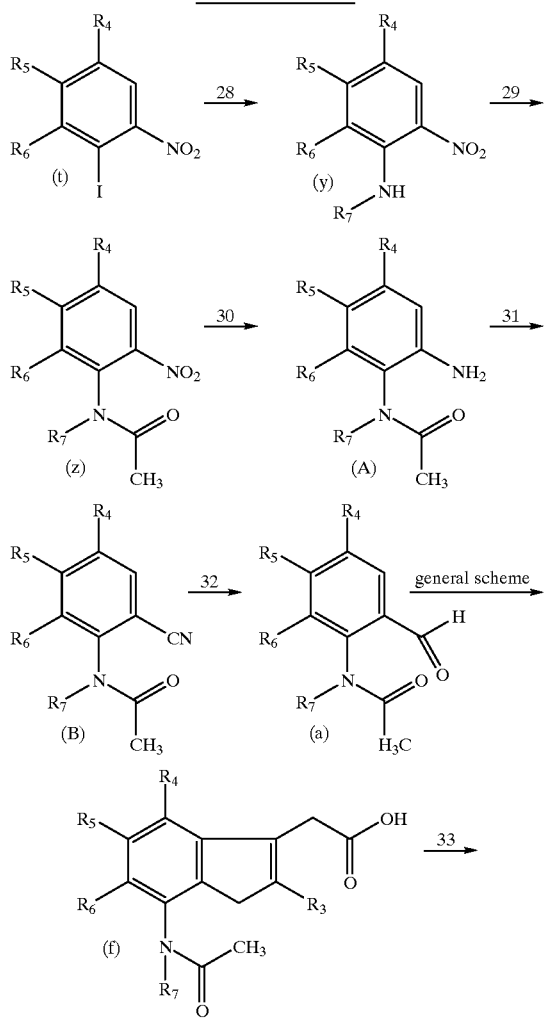

-continued

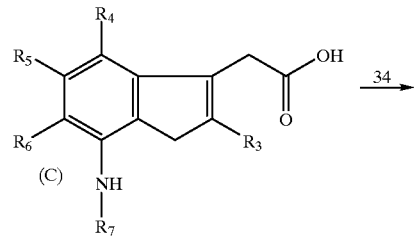

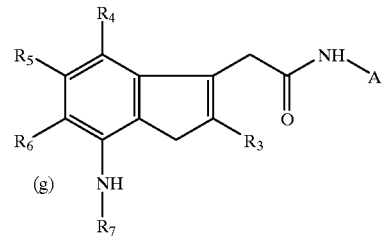

The substituted iodo-nitrobenzene (t) is charged with the amine $R_7$-$NH_2$ in the presence of copper in dimethylformamide and potassium carbonate (reaction 28). The secondary amine is protected by acetylation with acetic anhydride in pyridine (reaction 29). The nitro group of the amide (z) is reduced with hydrogen over palladiun-charcoal (reaction 30). The aniline derivative (A) is charged with $NaNO_2$ and sulfuric acid, followed by copper cyanide (reaction 31), to obtain the nitrile (B), which is heated (reaction 32) with formic acid in the presence of Raney-nickel to give the aldehyde (a). Following the general scheme, the amine-substituted indenyl acetic acid (f) is obtained. The N-protecting acetyl group is removed (reaction 33) by refluxing with concentrated hydrochloric acid in alcohol. The amine-substituted acid (C) is aminated by reaction with coupling reagents (e.g., DCC) and amine to yield the amide (g) (reaction 34).

The reagents and conditions of scheme V are as follows:

28. $R_7$-$NH_2$, $Cu^0$, DMF, $K_2CO_3$
29. Pyridine, $Ac_2O$
30. $H_2$, Pd/C
31. a) $NaNO_2$, $H_2SO_4$
    b) CuCN
32. HCOOH, Raney-Ni, temp.
33. Conc. HCl, alcohol, temp.
34. a) coupling reagent (e.g. DCC)
    b) amine If X is —O—S(O)$_2$—, the following scheme VI is employed to obtain the aldehyde (a).

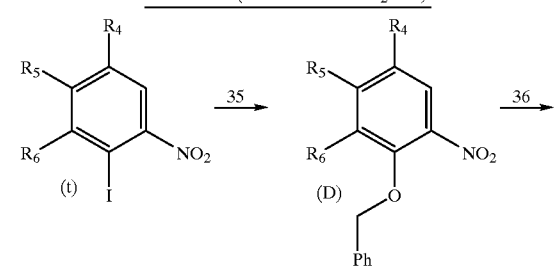

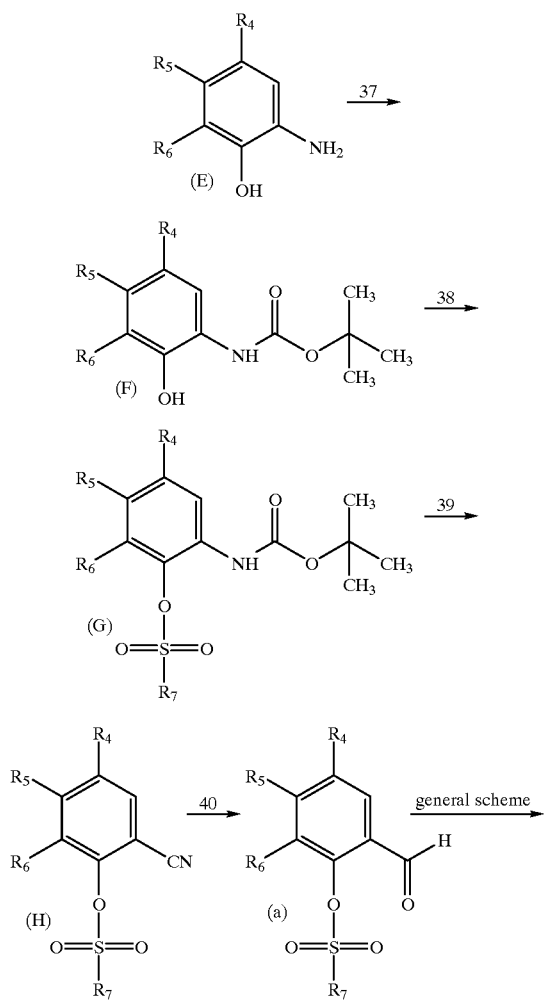

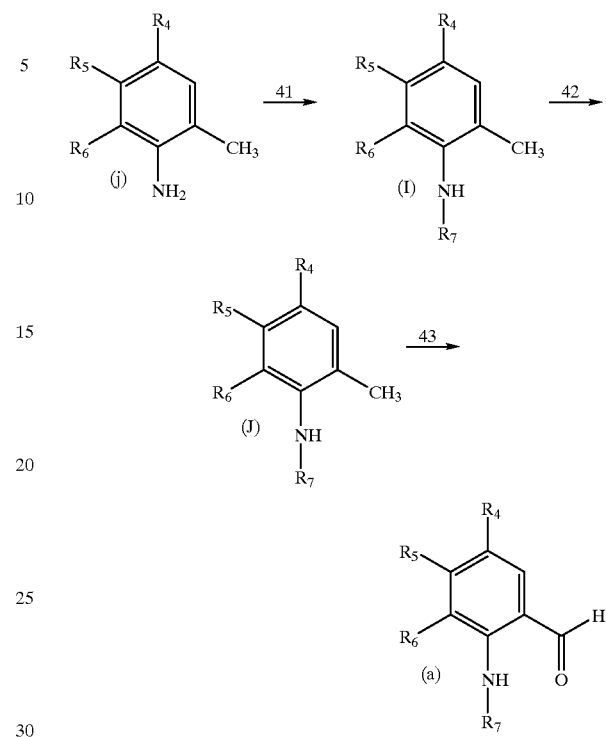

The substituted iodo-nitrobenzene (t) is charged with sodium benzyl alcoholate to obtain compound (D) (reaction 35), which is reduced with hydrogen over palladium/charcoal to the 2-amino-phenol derivative (E) (reaction 36). The amino group is protected (compound (F)) by reaction with BOCON (reaction 37) and the sulfonylchloride derivative $R_7$—S(O)$_2$-Cl is added to give compound (G) (reaction 38). The protective group is removed by reaction with $NaNO_2$ and $H_2SO_4$ and subsequent reaction with copper cyanide (reaction 39) gives the cyano-substituted derivative (H). The cyano group of compound (H) is transformed with HCOOH/Raney-nickel to the aldehyde (a) (reaction 40).

The reagents and conditions of scheme VI are as follows:
35. Ph—CH$_2$—ONa
36. H$_2$, Pd/C
37. BOCON
38. R$_7$—S(O)$_2$-Cl
39. a) NaNO$_2$, H$_2$SO$_4$
    b) CuCN
40. HCOOH, Raney-Ni If X is a tertiary amine NR-R$_7$, the following scheme VII is used.

The amino group of the toluene derivative (j) is substituted with a halide R$_7$-Hal to the secondary amine (I) (reaction 41). Reaction 42 with sodium hydride and the halogenide R-Hal yields the tertiary amine (J). The methyl group of compound (J) is transformed to the aldehyde (a) by reaction with CrO$_3$ and acetic acid (reaction 43).

The reagents and conditions of scheme VII are as follows:
41. R$_7$—Cl
42. NaH, R—Cl
43. CrO$_3$, CH$_3$COOH If X is an amide —NR—C(O)—R$_7$, the following scheme VIII is used.

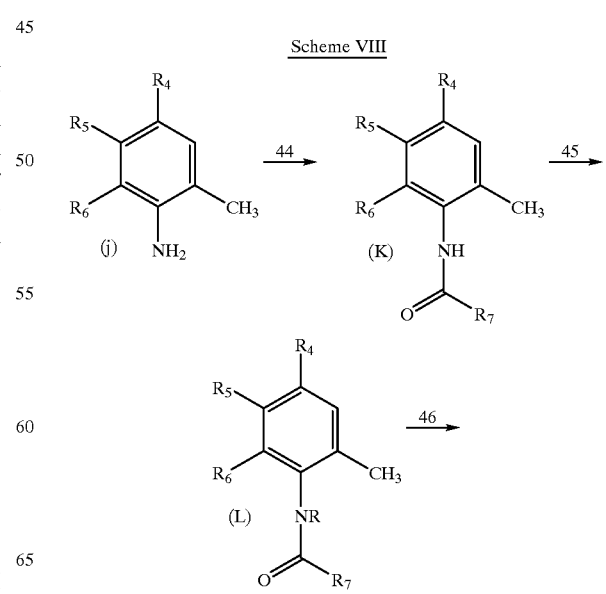

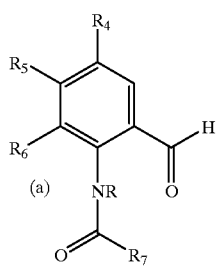

The amino group of the toluene derivative (j) is substituted with an acid halide $R_7$—C(O)-Hal to the amide (K) (reaction 44). Reaction 45 with sodium hydride and the halogenide R-Hal yields the amide (L). The methyl group of compound (L) is transformed to the aldehyde (a) by reaction with $CrO_3$ and acetic acid (reaction 46).

The reagents and conditions of scheme VIII are as follows:

44. $R_7$—C(O)—Cl
45. NaH, R—Cl
46. $CrO_3$, $CH_3COOH$

If X is a substituted sulfonamide —NR—S(O)$_2$—$R_7$, the following scheme IX is used.

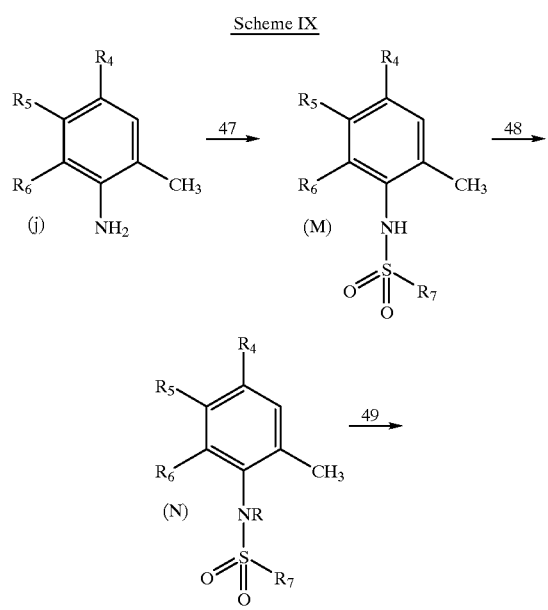

The amino group of the toluene derivative (j) is substituted with a sulfonyl halide $R_7$—S(O)$_2$-Hal to the sulfonylamide (M) (reaction 47). Reaction 48 with sodium hydride and the halide R-Hal yields the secondary sulfonylamide (N). The methyl group of compound (N) is transformed to the aldehyde (a) by reaction with $CrO_3$ and acetic acid (reaction 49).

The reagents and conditions of scheme IX are as follows:

47. $R_7$—S(O)$_2$—Cl
48. NaH, R—Cl
49. $CrO_3$, $CH_3COOH$

If X is a substituted sulfonic ester —S(O)$_2$—O—$R_7$, the following scheme X is used.

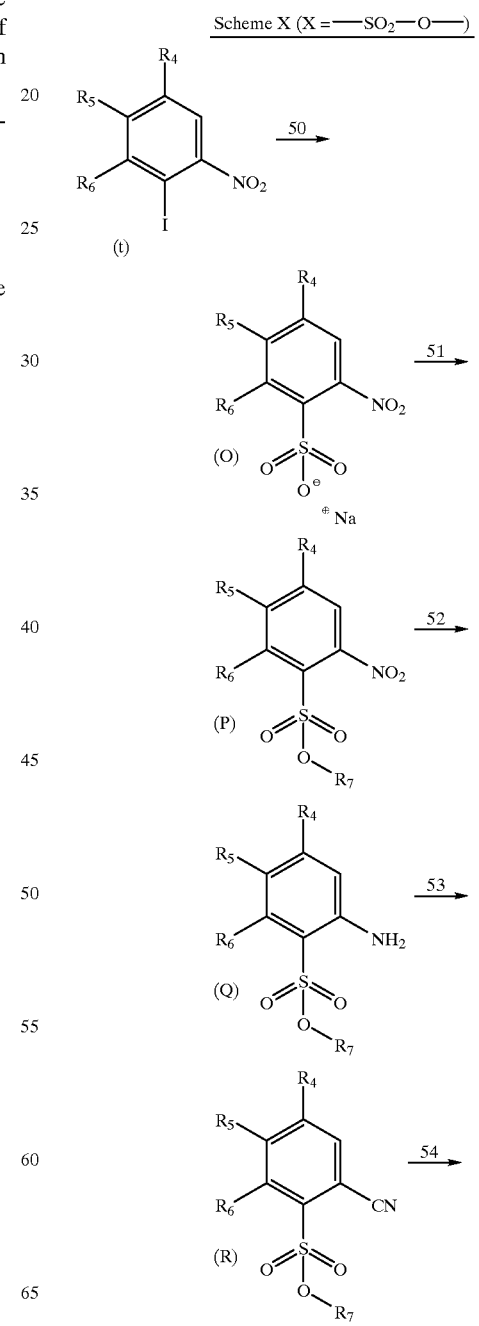

-continued

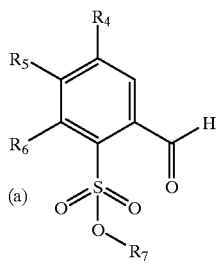

(a)

The substituted iodo-nitrobenzene (t) is charged with sodium sulfite to obtain compound (O) (reaction 50). The sodium salt (O) is allowed to react with the halide $R_7$-Hal to obtain the 2-nitro-substituted sulfonic ester (P), which is reduced with hydrogen over palladium/charcoal to the 2-amino-substituted sulfonic ester derivative (Q) (reaction 52). The amino group is transformed to a cyano group by reaction with $NaNO_2$ and $H_2SO_4$ and subsequent reaction with copper cyanide (reaction 53). The cyano group of compound (R) is allowed to react with HCOOH/Raney-nickel to the aldehyde (a) (reaction 54).

The reagents and conditions of scheme X are as follows:
50. Sodium sulfite
51. $R_7$-Hal
52. $H_2$, Pd/C
53. a) $NaNO_2$, $H_2SO_4$
    c) CuCN
54. HCOOH, Raney-Ni If X is a substituted ester —C(O)—O—$R_7$ or amide —C(O)—NH—$R_7$, the following scheme XI is used.

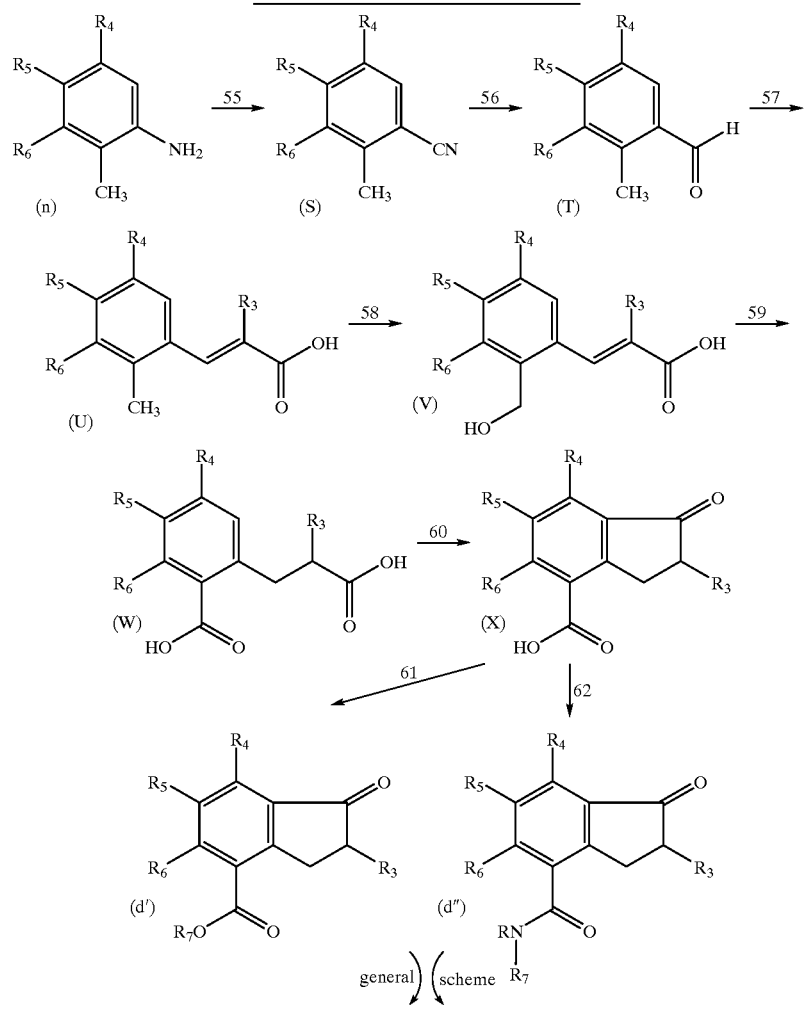

60
The 2-amino-toluene (n) is allowed to react with $NaNO_2$ and $H_2SO_4$, followed by copper cyanide (reaction 55) to give the cyano-derivative (S), which is then heated with formic acid over Raney-nickel to obtain the aldehyde (T) (reaction 56). The latter (T) is heated with propionic anhydride and sodium propionate to give a cinnamic acid derivative (U) (reaction 57). A radical reaction with N-bromo-succinimide, followed by the reactions with triethylammnonium formiate and then with hydrochloric acid (reaction 58) leads to the benzyl alcohol derivative (V). The double bond of the cinnamic acid rest is reduced with hydrogen over palladium/charcoal at 1 atm and the alcohol is oxidized with KMnO$_4$ to the carboxylic acid derivative (W) (reaction 59). Reaction with oxalyl chloride, aluminium trichloride and water gives the indanone (X) (reaction 60). The latter (X) is charged with oxalyl chloride and an alcohol R$_7$-OH (reaction 61) to obtain the ester (d') or it is charged with oxalyl chloride and a secondary amine R$_7$RNH (reaction 62) to obtain the amide (d"). Both compounds (d') and (d") then undergo a Refornatsky reaction and follow the procedure described in the general scheme.

The reagents and conditions of scheme X are as follows:

55. a) NaNO$_2$, H$_2$SO$_4$
    b) CuCN
56. HCOOH, Raney-Ni
57. propionic anhydride, sodium propionate, 135° C.
58. a) N-bromo-succinimide
    b) Et$_3$NH$^+$HC(O)O$^-$
    c) HCl
59. a) H$_2$, Pd/C, 1 atm
    b) KMnO$_4$
60. a) oxalyl chloride
    b) AlCl$_3$
    c) Water
61. a) oxalyl chloride
    b) R$_7$OH
62. a) oxalyl chloride
    b) R$_7$RNH If X is an ether —O—$_7$, the following scheme XII is used.

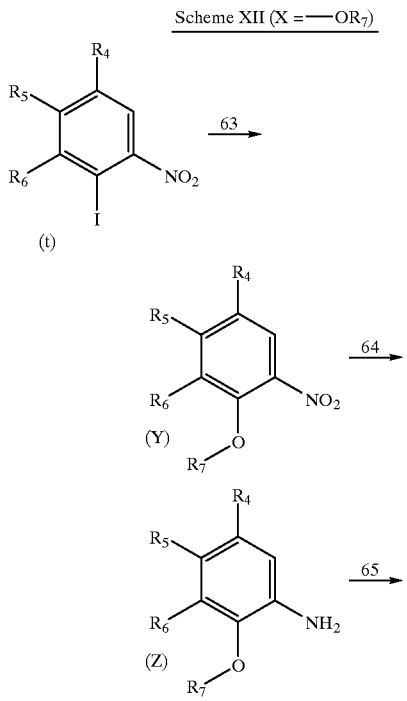

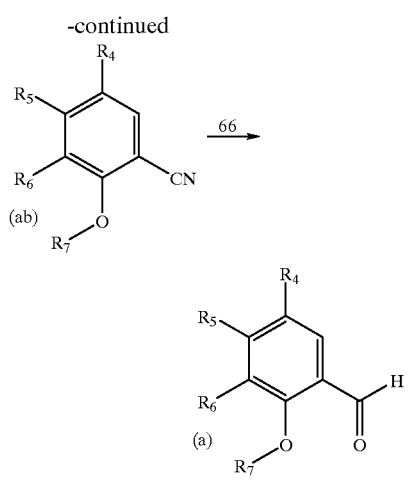

The substituted iodo-nitrobenzene (t) is charged with a sodium alcoholate R$_7$ONa to obtain compound (Y) (reaction 63), which is reduced with hydrogen over palladium/charcoal to the aniline derivative (Z) (reaction 64). The amino group is transformed to a cyano group by reaction with NaNO$_2$ and H$_2$SO$_4$ and subsequent reaction with copper cyanide (reaction 65). The cyano group of compound (ab) is allowed to react with HCOOH/Raney-nickel to the aldehyde (a) (reaction 66).

The reagents and conditions of scheme XII are as follows:

63. R$_7$-ONa
64. H$_2$, Pd/C
65. a) NaNO$_2$, H$_2$SO$_4$
    d) CuCN
66. HCOOH, Raney-Ni If X is an ether —CH$_2$—O—R$_7$, the following scheme XIII is used.

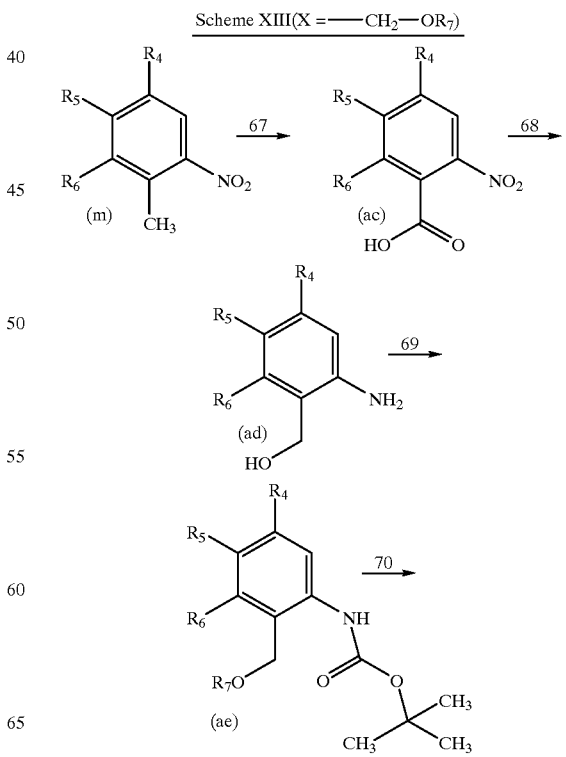

-continued

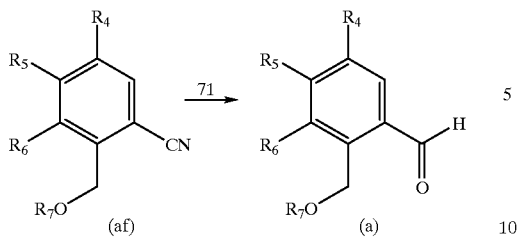

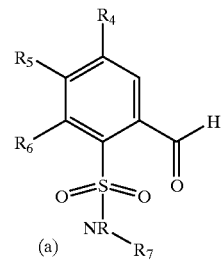

The substituted nitrotoluene (m) is charged with a potassium permanganate to obtain the benzoic acid derivative (ac) (reaction 67), which is reduced with lithium aluminium hydride to the amino-benzylalcohol-derivative (ad) (reaction 68). The amino group is protected by reaction with BOCON, and the reaction with silveroxide and a halide $R_7Hal$ leads to the ether (ae) (reaction 69). The latter (ae) is charged with $NaNO_2$ and $H_2SO_4$ and subsequently with copper cyanide (reaction 70) to yield the cyano-substituted compound (af) (reaction 71). The cyano group of compound (af) is allowed to react with HCOOH/Raney-nickel to the aldehyde (a) (reaction 71).

The reagents and conditions of scheme XIII are as follows:
67. $KMnO_4$
68. $LiAlH_4$
69. a) BOCON
    b) $Ag_2O$, $R_7Cl$
70. a) $NaNO_2$, $H_2SO_4$
    b) CuCN
71. HCOOH, Raney-Ni If X is a sulfonamide —$S(O)_2$—NR—$R_7$, the following scheme XIV is used.

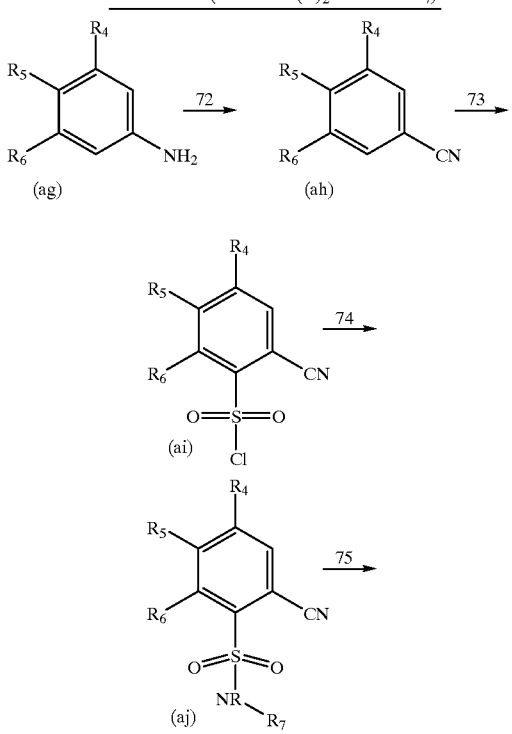

The aniline (ag) is charged with $NaNO_2$ and $H_2SO_4$, and subsequently with copper cyanide (reaction 72) to yield the cyano-substituted compound (ah). Compound (ah) is allowed to react with chloro sulfonic acid to yield a sulfonyl chloride (ai) (reaction 73).

The substitution at the sulfonyl group is performed with a secondary amine $R_7RNH$ (reaction 74) to give compound (aj). The cyano group of compound (aj) is allowed to react with HCOOH/Raney-Nickel to the aldehyde (a) (reaction 75).

The reagents and conditions of scheme XIV are as follows:
72. a) $NaNO_2$, $H_2SO_4$
    b) CuCN
73. Cl—$S(O)_2$OH
74. $R_7RNH$
75. HCOOH, Raney-Ni

EXAMPLE 1

6-Fluoro-2-Methyl-4-(4-Methylsulfinylphenyl)-Indenyl-1-Acetic Acid

A. 4-Fluoro-2-Nitrotoluene

4-Fluorotoluene (14 g) is added slowly with stirring to a solution of fuming nitric acid (18 g) and concentrated sulfuric acid (30 g) over 30 minutes and alternately warmed and cooled to keep the temperature between 40 and 50° C. This is followed by heating at 100° C. for 30 minutes more. The organic material is cooled and extracted with methylene chloride to give 16 g of 4-fluoro-2-nitrotoluene.

B. 5-Fluorotoluidine

The above nitrotoluene is hydrogenated in ethanol (200 ml) over one teaspoonifl of Raney Nickel catalyst with hydrogen at 42 p.s.i. and room temperature. When the theoretical amount of hydrogen has been taken up, the hydrogenation is stopped, and the catalyst carefully filtered off. The filtrate is evaporated to dryness to yield an oil which is distilled.

C. 4—Chloro-5'-Fluoro-2'-Methylbiphenyl

The toluidine is diazotized as in reference Cadogan J. Chem. Soc. 4257 (1962), using amyl nitrate and added at 40° C. to chlorobenzene as reactant and solvent with a small amount of bright copper powder. The reaction is then stirred at 70° C. for 8 hours, poured into dilute hydrochloric acid and extracted with chloroform. The $CHCl_3$ layer is washed with water, separated, dried ($MgSO_4$) and filtered. The crude product is put on a column of silica-gel (Baker Analysed 60–200 mesh, 2 ft.×2 in.). Elution with n-hexane gives pure 4-chloro-5'-fluoro-2'-methylbiphenyl.

D. 4-Chloro-5'-Fluoro-2'-Formylbiphenyl

Bromine (67 g) is added slowly to a stirred solution of 4-chloro-5'-fluoro-2'-methylbiphenyl (of 46.9 g) while being illuminated. The temperature is kept between 105–110° C. for 1 hour. Water (120 ml) and calcium carbonate (90 g) are then added to this product with stirring at reflux for 20 hours.

The organics are extracted with chloroform (400 ml.), and the organic phase is washed with water, separated and dried (MgSO₄). The chloroform is evaporated. The residue is recrystallized from hexane.

E. 5'-Fluoro-2'-Formyl-4-Methylthiobiphenyl

85% potassium hydroxide solution (66 g) is dissolved in ethanol (700 ml) and cooled to room temperature. To this with stirring is added methyl mercaptan subsurface (50 g), water (2ml) and a solution of 4-chloro-5'-fluoro-2'-formylbiphenyl (234.5 g) in ethanol (300 ml). A slow stream of methyl mercaptan is continuously fed in while the reaction mixture is held at reflux for 3 hours. The reaction is poured into water (1 liter), and the solid is filtered off. The solid is recrystallized from benzene.

F. 5'-Fluoro-2'-Formyl-4-Methylsulfinylbiphenyl

The above product 5-fluoro-2'-formyl-4-methylthiobiphenyl (123 g) in isopropanol (1 liter) is cooled to 5° C. with an ice bath and poured into 30% hydrogen peroxide (220 g) and stirred overnight. Excess peroxide is destroyed, the isopropanol stripped off, the product extracted with methylene chloride (6 times 500 ml.) and the organic phase is dried (MgSO₄). The drying agent is filtered off, and the solvent is evaporated to give 5'-fluoro-2'-formyl-4-methylsulfmylbiphenyl. The solid is recrystallized from benzene.

G. 3-[4-Fluoro-2-(4'-Methylsulfinylbiphenyl)-α-methyl cinnamic acid

The last reaction product 5'-fluoro-2'-formyl-4-methylsulfinylbiphenyl (262 g), propionic anhydride (160 g) and sodium propionate (96 g) are heated at 135° C. for 8 hours. The reaction mixture is poured onto 2 liters of water. The precipitate is redissolved on adding saturated potassium carbonate (2.5 liters). The warm solution is extracted with of toluene (2 times 500 ml.), and the aqueous layer carefully acidified with concentrated hydrochloric acid and ice. The solid acid is collected and dried at 100° C. over calcium chloride.

H. 3-[4-Fluoro-2-(4'-Methylsulfinylbiphenyl)]-α-methyl propionic acid

The above dried product 3-[4-Fluoro-2-(4'-methylsulfinylbiphenyl)-α-methyl cinnamic acid (300 g), PtO₂ (5 g) in ethylacetate (3 liters) is hydrogenated at 42 p.s.i. and room temperature until the theoretical uptake of hydrogen has been completed. The catalyst is filtered off and the solvent evaporated to dryness. The crude solid is collected.

I. 6-Fluoro-4-(4'-Methylsulfinylbiphenyl)-2-Methylindanone

The above dried product 3-[4-Fluoro-2-(4'-methylsulfinylbiphenyl)]-α-methyl propionic acid (60 g) is added to polyphosphoric acid (1 kg). The mixture is stirred on the steam bath for 4 hours and then poured onto ice-water. The precipitate is collected and dried.

J. Methyl 6-Fluoro-2-Methyl-4-(4-Methylsulfinylphenyl)-indenyl-1-acetate

A mixture of the indanone (30.2 g), zinc dust (8.0 g), methyl bromoacetate (15.2 g) in dry benzene (1 liter) is stirred with a crystal of iodine at reflux for 4 to 5 hours. The reaction mixture is poured onto 5% sulfuric acid (500 ml.), separated and dried (MgSO₄). The filtrate is refluxed with phosphorous pentoxide (60 g) for 2 hours and is decanted. The organic layer is washed with saturated bicarbonate solution and water. After drying and evaporating of the benzene, the ester is recrystallized from benzene.

K. 6-Fluoro-2-Methyl-4-(4-Methylsulfinylbiphenyl)-indenyl-1-Aacetic acid

The above ester methyl 6-fluoro-2-methyl-4-(4-methylsulfinylphenyl)-indenyl-1-acetate (10 g) is refluxed in 1:1 ethanol-water (200 ml) containing sodium hydroxide (4 g) for 1 hour, cooled, the alcohol is evaporated off, extracted with ethyl acetate (2 times 100 mnl.) and the aqueous layer is acidified with hydrochloric acid. The precipitated solid is filtered off, dried and recrystallized from ethyl acetate.

Similarly, when one of the following toluene compounds: 4-chloro toluene, 4-methoxy toluene, 2-fluoro toluene, 3-fluoro toluene, toluene, xylene, 4-dimethylaminotoluene, 4-acetyloxytoluene (except for cyanoacetic acid preparation), 4-vinyltoluene, 4-vinyloxytoluene, 4-methylthiotoluene, 3-methylthiotoluene, 3-benzyloxytoluene or 4-methylsulfinyltoluene is used in place of 4-fluorotoluene in Example 1 A above and the product carried through Examples 1 B–K, the corresponding appropriately substituted indenyl-1-acetic acids are obtained.

Similarly, when benzene, fluorobenzene, methylthiobenzene, hydroxybenzene, methoxybenzene or acetylbenzene is used in place of chlorobenzene in Example 1 C and it is also used in excess as a solvent and the product is carried through Examples 1 D and G–K, the corresponding 6-fluoro-2-methyl-4-(substituted phenyl)-indenyl-1-acetic acid compound is obtained.

Similarly, when Example 1 is carried out with the omission of Example 1 F, 6-fluoro-2-methyl-4-(p-methylthiophenyl)-indenyl-1-acetic acid is obtained.

L. Alternate procedure for Reaction 1 I

A solution of 3-[4-Fluoro-2-(4'-methylsulfinylbiphenyl)-α-methyl propionic acid (64 g) in thionyl chloride (600 ml) is stirred for 90 minutes and is refluxed for 30 minutes. The solution is evaporated to dryness and added in carbon disulfide (100 ml) to a suspension of anhydrous aluminum chloride (60 g) in carbon disulfide (250 ml.) at <10° C. with stirring. The reaction is stirred at 25° C. for 12 hours, poured into 2.5 N hydrochloric acid crushed ice (2 liter) with stirring. Ether (1 liter) is added and when all is dissolved, the ether layer is separated and dried (MgSO₄). Evaporation of the ether gives the desired indanone, 6-fluoro-4-(4'-methylsulfinylbiphenyl)-2-methylindanone.

M. Alternate procedure for Reactions I, J and K combined

A mixture of 6-fluoro-2-methyl-4-(4'-methylsulfinylbiphenyl) indanone (30.2 g), cyanoacetic acid (10.5 g), acetic acid (6.6 g.) and ammonium acetate (1.7 g) in dry toluene (20 ml.) is refluxed with stirring for 24 hours while the water is removed continuously in a Dean-Stark trap. The toluene is concentrated, the residue is dissolved in 4 N potassium hydroxide solution (200 ml), 100 ml. ethanol, 100 ml. water and refluxed for 12 hours. The solution is concentrated in vacuo in order to remove the ethanol. The aqueous layer is filtered and is acidified with concentrated HCl. The precipitated 6-fluoro-2-methyl-4-(4-methylsulfinylphenyl)-indenyl-1-acetic acid is collected and is dried at 70° C. in the vacuum oven.

EXAMPLE 2

(Z,E)-5-Fluoro-2-Methyl-7-(p-Methylsulfinylstvryl)-Indenyl-3-Acetic Acid

A. 5-Fluoro-2-Nitrotoluene

3-Fluorotoluene (1 mole) in concentrated sulfuric acid (200 ml.) is stirred at 0° C. while a cold solution of potassium nitrate (1.5 mole) in concentrated sulfuric acid (750 ml.) is added slowly during 3 hours, the temperature being kept below 5° C. with an ice-ethanol bath After the addition is complete, the ice-bath is removed and stirring is continued for 3 hours at room temperature. Water (400 ml.) is added, and the organic layer is separated, dried (MgSO₄) and filtered. The oil is separated by vapor-phase chromatograph on a 200×1 cm. silicone oil column (DC 200 20%) on Chromosorb R (60/80) at 191° C. and a helium flow rate of 86 ml./min. The desired pure nitro-isomer is collected.

B. 4-Fluoro-2-Toluidine

5-Fluoro-2-nitrotoluene (0.5 mole) in ethyl acetate (600 ml.) is hydrogenated at 40 p.s.i. of hydrogen over Pd/C catalyst (1%, 2 teaspoons) at room temperature until the theoretical amount of hydrogen has been taken up. The catalyst is filtered off, and the solvent evaporated to give the crude oil of 4-fluoro-2-toluidine.

C. 4-Fluoro-2-Toluidinylbromide

Bromine (0.5 mole) is added over 1 hour to stirred 4-fluoro-2-toluidine (0.5 mole) at 100° C. illuminated with a high wattage lamp. The crude benzyl bromide is used as prepared.

D. 4-Fluoro-2-Toluidinyl Triphenylphosphonium bromide

The above benzylhalide (0.2 mole) and triphenylphosphine (0.2 mole) are heated at 100° C. for 4 hours in dry dimethylformamide. The precipitated phosphonic salt is collected and recrystallized from ethanol.

E. (Z,E)-5-Fluoro-4'-Methylsulfinyl-2-Amino stilbene

To a stirred solution of the above salt (0.1 mole) in tetrahydrofuran (200 ml.) at 10–15° C. is added a solution of n-butyl lithium (21.9% in hexane; 0.11 mole) under nitrogen and the stirring continued for 2 hours. To this solution with stirring is then added p-methylsulfinylbenzaldehyde (0.1 mole) in tetrahydrofuran (50 ml.) at 10° C. over 20 minutes under nitrogen. Saturated ammonium chloride solution (100 ml.) is run into the reaction after 1 hour at room temperature. The organic layer is separated, dried (MgSO$_4$), filtered and evaporated to yield an oil which is a mixture of (Z,E)-5-fluoro-4'-methylsulfinyl-2-amino stilbenes. These compounds are then separated on the same preparative vapor phase chromatograph column mentioned in Part A above.

F. (Z,E)-5-Fluoro-4'-Methylsulfinyl-2-Cyano stilbene

A fresh sample of cuprous cyanide is prepared from copper sulphate (65 g) in water (205 ml.) sodium bisulfide (18 g) in water (52 ml.) and potassium cyanide (18 g.) in water (52 ml.). The precipitated cuprous cyanide is dissolved in a solution of sodium cyanide (26 g) in water (65 ml.).

The above aniline (0.5 mole) and sodium nitrite (0.55 mole) in hydrochloric acid are added, the temperature is kept below 5° C.

The solution of the diazonium chloride is added to the cold solution of the cyanides and the temperature is brought up to between 60–70° C. and is kept there for 1 hour. The precipitate is collected, is washed well with water and dried. The solid is recrystallized from n-hexane to give the pure (Z,E)-cyano stilbene isomers.

G. (Z,E)-5-Fluoro-4'-Methylsulfinyl stilbene-2-Aldehyde

The nitrile isomers (0.2 mole) are refluxed in 75% formic acid (1. 5 1.)with Raney nickel (50 g) at 125° C. for 3 hours. The reaction mixture is evaporated to ¼ volume, and the organic aldehydes are extracted with methylene chloride solution. The organic layer is dried (MgSO$_4$), filtered and evaporated to yield the (Z,E)-5-fluoro-4'-methylsulfinyl stilbene-2-aldehyde.

H. (Z,E)-5-Fluoro-2-Methyl-7-(Methylsulfinylstyryl)-indenyl-3-Acetic acid

The compound of Part G above is reacted in the same proportions in accordance with Steps G–K of Example 1 to yield (Z,E)-5-fluoro-2-methyl-7-(4-methylsulfinylstyryl)-indenyl-3-acetic acid. The geometrical isomers can be separated via chromatography.

Similarly, when 3-chlorotoluene, 3-dimethylaminotoluene, 3-acetyloxytoluene, 3-vinyltoluene, 3-vinyloxytoluene, 4-methoxytoluene, 2-chlorotoluene, toluene, 3-methylthiotoluene, 4-benzyloxytoluene, 2-xylene or 3-methylsulfinyltoluene are used in place of 3-fluorotoluene in Example 2 A above, and the product reacted in accordance with Example 2 B–H, there are obtained the geometrical isomers of the corresponding substituted 7-(4-methylsulfinyl styryl)-indenyl-3-acetic acid.

Similarly, when Example 2 is carried out using 4-methylthiobenzaldehyde, 4-hydroxybenzaldehyde, 3-methoxybenzaldehyde, benzaldehyde, 4-fluorobenzaldehyde, 2-chlorobenzaldehyde, 4-acetylaminobenzaldehyde, 4-acetylbenzaldehyde or 2-methylbenzaldehyde in place of 4-methylsulfinylbenzaldehyde in Example 2 E, the corresponding geometrical isomers of 5-fluoro-2-methyl-7-(substituted styryl)-indenyl-3-acetic acid are obtained.

EXAMPLE 3

5-Fluoro-2-Methyl-7-(p-Methylsulfinylbenzoyl)-Indenyl-3-Acetic Acid

A. 5-Fluoro-2-Methyl-4'-Methylsulfinylbenzophenone

4-Methylsulfinylbenzoyl chloride (0.2 mole) and 4-fluorotoluene (0.2 mole) are refluxed together in trifluoromethanesulfonic acid for 6 hours according to the procedure of Chodroff and Klein, J.A.C.S. 70, 7209 (1948). In this way, 5-fluoro-2-methyl 4'-methylsulfinylbenzophenone is made and isolated.

B. 4-Fluoro-2-(4-Methylsulfinylbenzoyl)benzal bromide

The procedure of Example 2 C is carried out using an equivalent amount of 5-fluoro-2-methyl-4'-methylsulfinylbenzophenone in place of 5-fluoro-o-toluidine and 1.0 mole of bromine to obtain the above compound.

C. 4-Fluoro-2-(P-Methylsulfinylbenzoyl) Benzaldehyde

The benzal bromide prepared above is refluxed for 20 hours with calcium carbonate (90 g.) in water (120 ml.). The reaction mixture is then steam-distilled, and the oil distillate dried (Magnesium sulfate). Evaporation of the solvent yields crude aldehyde which is recrystallized from benzene.

D. 5-Fluoro-2-Methyl-7-(P-Methylsulfinylbenzoyl)-indenyl-3-Acetic acid

The procedure of Example 1 G is used employing an equivalent amount of 4-fluoro-2-(4-methylsulfinylbenzoyl) benzaldehyde in place of 5'-fluoro-2'-formyl-4-methylsulfinylbiphenyl and the product therefrom is reacted in accordance with Example 1, Steps H–K to obtain 5-fluoro-2-methyl-[4-methylsulfinylbenzoyl)-indenyl-3-acetic acid.

Similarly, when an equivalent amount of 4-methylthiobenzoylchloride, 4-hydroxybenzoylchloride, 3-methoxybenzoylchloride, 4-fluorobenzoylchloride, 2-chlorobenzoylchloride, 4-acetylaminobenzoylchloride, 4-acetylbenzoylchloride or 2-methylbenzoylchloride is used in place of 4-methylsulfinylbenzoyl chloride in Example 3 A above and the product is reacted in accordance with Example 3, Steps B–D, there is obtained the corresponding 5-fluoro-2-methyl-7-(substituted benzoyl)-indenyl-3-acetic acid.

Similarly, when an equivalent amount of 4-chlorotoluene, 4-methoxytoluene, 2-fluorotoluene, 3-fluorotoluene, toluene, xylene, 4-dimethylaminotoluene, 4-acetyloxytoluene, 4-vinyltoluene, 4-vinyloxytoluene, 4-methylthiotoluene, 3-methylthiotoluene, 3-benzyloxytoluene, 4-methylsulfinyltoluene or 2-methylthiotoluene is used in place of 4-fluorotoluene in Example 3 A above and the product is reacted in accordance with Example 3, Steps B–D, the corresponding substituted 2-methyl-7-(4-methylsulfinylbenzoyl)-indenyl-3-acetic acid is obtained.

EXAMPLE 4

5-Fluoro-2-Methyl-7-(4-Methylsulfinylphenethynyl)-Indenyl-3-Acetic Acid

A. 5-Fluoro-4'-Methylsulfinyl-2-Amino-diphenylacetylene

To the product from Example 2 E (Z,E)-5-fluoro-4'-methylsulfinyl-2-amino-stilbene (0.1 mole) in chloroform (200 ml.) is added bromine (0.2 mole) dropwise over 2 hours at 0° C. The solvent is evaporated, and the product is refluxed in 10% sodium ethoxide in ethanol (400 ml.) under nitrogen overnight. The product is evaporated to dryness and extracted with ethyl acetate (4×200 ml.). The ethyl acetate is distilled off, and the residue is fractionally distilled to give pure 5-fluoro-4'-methylsulfinyl-2-amino-diphenylacetylene.

B. 5-Fluoro-2-Methyl-7-(4-Methylsulfinylphenethynyl)-indenyl-3-Acetic acid

An equivalent amount of the product of Example 4 A is used in place of (Z,E)-5-fluoro-4'-methylsulfinyl-2-aminostilbene in Example 2 F above, and the product therefrom is reacted in accordance with Example 2, G–H, to obtain 5-fluoro-2-methyl-7-(4-methylsulfinylphenylethynyl)-indenyl-3-acetic acid.

Similarly, when th ther 2-aminostilbenes obtained from Example 2 are used in place of (Z,E)-5-fluoro-4'-methylsulfinyl-2-amino-stilbene in Example 4 A above, and the product therefrom is reacted in accordance with Example 4 B, the appropriately substituted 2-methyl-7-phenylethynyl-indenyl-3-acetic acids are obtained.

EXAMPLE 5

5-Fluoro-2-Methyl-7-(4-Methylsulfinylphenylethyl)-Indenyl-3-Acetic Acid

A. 5-Fluoro-4'-Methylsulfinyl-2-Aminodiphenyl ethane

The product from Example 2 E, (Z,E)-5-fluoro-4'-methylsulfinyl-2-aminostilbene (0.2 mole) is hydrogenated over Pd/C 10% (2 g) in ethyl acetate (500 ml) at 40 p.s.i. of $H_2$ and room temperature until the theoretical amount of $H_2$ has been consumed. The catalyst is filtered off, and the solvent is evaporated to dryness.

B. 5-Fluoro-2-Methyl-7-(4-Methylsulfinylphenylethyl)-indenyl-3-Acetic acid

The product obtained from Example 5 A above is reacted in accordance with Example 2 F–H. to obtain the subject compound.

Similarly, when the other 2-aminostilbenes obtained from Example 2 are used in place of (Z,E)-5-fluoro-4'-methylsulfinyl-2-aminostilbene in Example 5 A above and the product therefrom is reacted in accordance with Example 5 B, the appropriately substituted 7-phenylethyl-indenyl-3-acetic acids are obtained.

EXAMPLE 6

5-Fluoro-2-Methyl-7-(p-Methylsulfinylbenzyl)-Indenyl-3-Acetic Acid

A. 5-Fluoro-4'-Methylsulfinyl-2-Methyldiphenyl methane

The product from Example 3 A, 5-fluoro-2-methyl-4'-methylsulfinylbenzophenone (0.2 mole), is refluxed in concentrated hydrochloric acid (100 ml.) with zinc amalgam (45 g) and water (30 ml.). Hydrogen chloride gas is slowly bubbled in during the reaction. After 2 to 3 hours, the gas supply is stopped and the product is steam distilled. The oily distillate is extracted into ether (3 times 300 ml.), washed with water (2×50 ml.), dried (MgSO$_4$), filtered and collected by evaporating the solvent. It is then fractionally distilled under reduced pressure to give pure 5-Fluoro-4'-methylsulfinyl-2-methyldiphenyl methane.

B. 5-Fluoro-2-Methyl-7-(P-Methylsulfinylbenzyl)-indenyl-3-Acetic acid.

The product of Example 6 A is reacted in accordance with the procedure of Example 3 B–D to yield the desired product.

Similarly, when the other substituted 4-methylsulfinylbenzophenones or 5-fluoro-2-methyl-4'-substituted benzophenones obtained from Example 3 are used in place of 5-fluoro-2-methyl-4'-methylsulfinylbenzophenone in Example 6 above, the corresponding substituted-7-(4-methylsulfinylbenzyl)-indenyl-3-acetic acid and 5-fluoro-2-methyl-7-(substituted benzyl)-indenyl-3-acetic acid, respectively are obtained.

EXAMPLE 7

N-Acetyl-5-Fluoro-2-Methyl-7-(4-Methylsulfinylanilino)-Indenyl-3-Acetic Acid

A. 5-Fluoro-4'-Methylsulfinyl-2-Nitrobiphenylarmine

2-Iodo-4-fluoronitrobenzene (0.2 mole) and 4-methylsulfinylaniline (0.2 mole) are refluxed in dry dimethylformamide (300 ml.) containing copper powder (5 g) and some powdered potassium carbonate (20 g) under nitrogen for 18 hours. The suspension is filtered, and the organics are washed with water (6 times 100 ml.) in benzene (600 ml.). The benzene layer is extracted with 2.5 N HCl (7×200 ml.), and the acid layer is poured onto powdered sodium bicarbonate. The basic solution is extracted with benzene (6 times 200 ml.), the benzene layer is washed with water (3 times 100 ml.), is separated, dried (MgSO$_4$) and filtered. Evaporation of the solvent followed by chromatography on a 2 in.×24 in. column of silica-gel (Baker), eluted with various proportions of benzene-hexane mixtures, gives pure 5-fluoro-4'-methylsulfinyl-2-nitrobiphenylamine.

B. N-Acetyl-5-Fluoro-4'-Methylsulfinyl-2-Nitrobiphenylamine

The above compound (0.5 mole) is stirred overnight at room temperature in pyridine (200 ml), with acetic anhydride (0.55 mole). The solution is evaporated to dryness at 5° C., is dissolved in dichloromethane (600 ml.) and is extracted with 2.5 N hydrochloric acid (6 times 200 ml.), and water (12×100 ml.); the dichloromethane layer is dried (MgSO$_4$). Filtering and evaporating to dryness gives N-acetyl-5-fluoro-4'-methylsulfinyl-2-nitrobiphenylamine.

C. N-Acetyl-5-Fluoro-2-Methyl-7-(4-Methylsulfinylanilino)-indenyl-3-Acetic acid

The compound from Example 7B above is reduced in accordance with the procedure of Example 2B to yield the corresponding amino compound. This compound in turn is reacted in accordance with the procedure of Example 2F to form the corresponding cyano compound is and further reacted in accordance with the procedure of Example 2G and H to form the desired N-acetyl 5-fluoro-2-methyl-7-(4-methylsulfinylanilino)-indenyl-3-acetic acid.

Similarly, when 4-chloroaniline, 4-methylaniline, 2-methoxyaniline, 4-methylthioaniline or 4-methylsulfonylaniline is used in place of 4-methylsulfinylaniline in Example 7A above and the product therefrom is carried through Example 7C, the corresponding N-acetyl-5-fluoro-2-methyl-7-(substituted anilino)-indenyl-3-acetic acid is obtained.

Similarly, when 2-iodo-4-chloronitrobenzene, 2-iodo-4-methoxynitrobenzene, 2-iodo-4-methylnitrobenzene or 2-iodo-3-methylnitrobenzene are used in place of 2-iodo-4- fluoronitrobenzene in Example 7A above, and the product therefrom is reacted in accordance with Example 7B–C, the corresponding N-acetyl-2-methyl-7-(p-methylsulfinylanilino)-substituted indenyl-3]-acetic acid is obtained.

EXAMPLE 8

5-Fluoro-2-Methyl-1-(4-Methylsulfinylanilino)-Indenyl-3-Acetic Acid

The product from Example 7 above (0.1 mole) in ethanol (120 ml.) and concentrated hydrochloric acid (100 ml.) is refluxed and stirred for 4 hours. Ethyl acetate and ethanol are removed on the rotary evaporator and the solution is poured onto solid sodium bicarbonate. The solution is acidified to a slightly acidic pH with glacial acetic acid and the precipitated acid is filtered off, dried and recrystallized from ethyl acetate.

EXAMPLE 9

N-Methyl-5-Fluoro-2-Methyl-7-(4-Methylsulfinylanilino)-Indenyl-3-Acetic Acid A. N-Methyl-5-Fluoro-4'-Methylsulfinyl-2-Nitrobiphenylamine The product from Example 7A (0.1 mole), aqueous formaldehyde (37% 0.11 mole) and formic acid (80% 0.11 mole) are refluxed for 4 hours, and the tertiary amine is extracted with chloroform (2×75 ml.). The chloroform solution is dried (MgSO$_4$), the organic solution filtered and evaporated to give N-methyl-5-fluoro-4'-methylsulfinyl-2-nitrobiphenylamine.

B. N-Methyl-5-Fluoro-2-Methyl-7-(4-Methylsulfinylanilino)-indenyl-3-Acetic acid

The reaction of Example 7 B through to the end is carried out on the above compound, Example 8A, to give N-methyl-5-fluoro-2-methyl-7-(4-methylsulfinylanilino)-indenyl-3-acetic acid.

EXAMPLE 10

5-Fluoro-2-Methyl-7-(4-Methylsulfinylphenylthio)-Indenyl-3-Acetic Acid

A. 5-Fluoro-4'-Methylsulfinyl-2-Nitrobiphenyl sulfide

4-Methylsulfinylthiophenol (0.2 mole) is dissolved in dry tetrahydrofuran (100 ml.) and sodium hydride (50% dispersion in mineral oil, 0.2 mole) is added over 30 minutes. The solution is evaporated to dryness and the residue is rinsed well with n-hexane. The powdered salt is stirred under N$_2$ at reflux with 4-fluoro-2-iodonitrobenzene (0.2 mole) in dry dimethylformamide for 16 hours, evaporated to dryness and extracted into chloroform (3 times 200 ml.). The organics are washed with water (2×100 ml.), separated and dried (MgSO$_4$). The solution is filtered, evaporated to dryness and put on a column of silica-gel (Baker 2 in. times 2 ft.) and various fractions are eluted with portions of benzene-n-hexane. In this way, pure 5-fluoro-4'-methylsulfinyl-2-nitrobiphenyl sulfide is obtained.

B. 4-Fluoro-2-(4-Methylsulfinylphenylthio)-aniline

The reaction described in Example 2 B is repeated on the product of Example 10A above to give the title compound.

C. 2-Cyano-5-Fluoro-4'-Methylsulfinylbiphenyl sulfide

The reaction described in Example 2 F is repeated on the product above to give the title compound.

D. 4-Fluoro-2-(4-Methylsulfinylphenylthio)benzaldehyde

The reaction described in Example 2 G is repeated on the above product to give the title compound.

E. 5-Fluoro-2-Methyl-7-(4-Methylsulfinylphenylthio)-indenyl-3-Acetic acid

The product from Example 10 D is reacted in accordance with the procedure of Example 2H to yield the desired compound.

Similarly, when 4-methylthiothiophenol, 4-methylthiophenol, 4-methoxythiophenol or 4-chlorothiophenol is used in place of 4-methylsulfinylthiophenol in Example 10A above and the product is carried through the reaction of Example 10B–E, the appropriate 5-fluoro-2-methyl-7-(substituted phenylthio)-indenyl-3]-acetic acids are obtained.

Similarly, when 4-methoxy-2-iodo-nitrobenzene, 4-methyl-2-iodo-nitrobenzene, or 4-chloro-2-iodo-nitrobenzene is used in place of 4-fluoro-2-iodo-nitrobenzene in Example 10A above and the product is reacted in accordance with Example 10B–E, the corresponding 2-methyl-7-(4-methylsulfinylphenylthio)-substituted indenyl-3]-acetic acids are obtained.

EXAMPLE 11

5-Fluoro-2-Methyl-7-(4-Methylsulfinylbenzoyl)-Indenyl-3-Acetamide

5-Fluoro-2-methyl-7-(4-methylsulfinylbenzoyl)-indenyl-3-acetic acid (0.01 mole) Example 3 is warmed with thionyl chloride (5 ml.) for 25 minutes. The mixture is cooled to 25° C. and poured with stirring into ice-cold concentrated ammonia solution. The precipitated amide is washed with water, dried and recrystallized from methanol-water to yield the subject compound.

Similarly when ammonia is replaced by an equivalent amount of the following amines, the corresponding amides can be obtained:

Morpholine,
Dimethylamine,
Ethanolamine,
Benzylamine,
N,N-diethylethylenediamine,
Benzylglycinate,
Piperidine,
Pyrrolidine,
N-methylpiperazine,
N-phenylpiperazine,
N-hydroxyethylpiperazine,
Piperazine,
Diethylamine,
Diethanolamine,
Aniline,
p-Ethoxyaniline,
p-Chloroaniline,
p-Fluoroaniline,
p-Trifluoromethylaniline,
Butylamine,
Cyclohexylamine,
Methylamine,
D-glucosamine,
Tetra-O-acetyl-d-glucosamine,
D-galactosylamine,
D-mannosylamine,
N,N-dimethylglycine amide, N,N-dibutylglycine amide,
N-methyl-2-aminomethylpiperidine,
N-methyl-2-aminomethylpyrrolidine,
β-Ethoxyethylamine,
Di(β-ethoxyethyl)amine,
β-Phenethylamine,
α-Phenethylamine,
Dibenzylamine or
D-mannosamine Similarly, when the other acetic acid compounds are used in place of an equivalent amount of 5-fluoro-2-methyl-4-(4-methylsulfinylbenzoyl)-indenyl-3-acetic acid in the above example, the corresponding amides are formed.

EXAMPLE 12

Ammonium-5-Fluoro-2-Methyl-7-(4-Methylsulfinylphenylethyl)-Indenyl-3-Acetate

To 5-fluoro-2-methyl-7-(4-methylsulfinylphenylethyl)-indenyl-3-acetic acid (0.001 mole) (example 5) in methanol (10 ml.) is added methanolic ammonia (1 N, 1 ml.). The mixture is evaporated to dryness to yield the subject compound.

EXAMPLE 13

Calcium-5-Fluoro-2-Methyl-7-(4-Methylsulfinylphenylethyl)-Indenyl-3-Acetate

To a slurry of 5-fluoro-2-methyl-7-(4-methylsulfinylphenylethyl)-indenyl-3-acetic acid (0.002 mole) (example 5) in water (10 ml.) is added hydrated calcium oxide (0.076 g., 0.001 mole) and the mixture is stirred for 15 minutes. The mixture is concentrated to dryness in vacuo, is slurried with methanol (10 ml.) and is again concentrated to dryness to yield the subject compound.

EXAMPLE 14

Aluminum-5-Fluoro-2-Methyl-7-(p-Methylsulfinylphenylethyl)-Indenyl-3-Acetate

To a solution of aluminum tert-butoxide (0.246 g., 0.001 mole) in ether (50 ml.) is added 5-fluoro-2-methyl-7-(4-methylsulfmylphenylethyl)-indenyl-3-acetic acid (0.003 mole) (example 5) in pyridine (50 ml.) with stirring at 10° C. The mixture is concentrated to dryness in vacuo to yield the subject compound.

EXAMPLE 15

6-Fluoro-2-Methyl-4-(4-Methylsulfonylphenyl)-Indenyll-1-Acetic Acid

A. 5'-Fluoro-2'-Formyl-4-Methylsulfonyl biphenyl
5'-Fluoro-2'-formyl-4-methylthiobiphenyl (10 mmol) (Example 1E) in THF (20 ml) is charged dropwise with oxone® (6 mmol) and tetrabutylammonium hydrogensulfate (1 mmol) in water (15 ml). The mixture is stirred at room temperature for 1 hour. The suspension is poured into water (300 ml), the precipitate is filtered off, is washed with water and is dried in vacuo to give the title product.

B. 6-Fluoro-2-Methyl-4(4-Methylsulfonylphenyl)-indenyl-1-Acetic acid

The procedure described in Example 1, parts G–K is followed with the above obtained 5'-fluoro-2'-formyl-4-methylsulfonyl biphenyl to yield the title product.

EXAMPLE 16

6-Fluoro-2-Methyl-4-(4-Pyridyl)Indenyl-1-Acetic Acid

A. 4-(5'-Fluoro-2'-Methyl-phenyl)pyridine
5-Fluorotoluidine (Example1,B), pyridine and pentyl nitrite are warmed until a vigorous reaction with evolution of gas sets in. This is allowed to proceed without heating until it has subsided (20 minutes) and the mixture is boiled under reflux for another 100 minutes. The excess pyridine is removed under reduced pressure to yield the title product.

B. 6-Fluoro-2-Methyl-4-(4-Pyridyl)indenyl-1-Acetic acid
The procedure described in Example 1 parts D–K is followed with the above obtained 4-(5-fluoro-2'-methyl phenyl) pyridine as the starting material to yield the title product.

EXAMPLE 17

When Example 2 is carried out using p-methylsulfonylbenzaldehyde, 4-pyridinecarboxaldehyde, 3-pyridine carboxaldehyde, 3-methylsulfonylbenzaldehyde, 2,3,4-trimethoxy benzaldehyde, 1,2,3-trimethoxy benzaldehyde, 2-furaldehyde, 3-furaldehyde, 3-thiophene carboxaldehyde, 2-thiophene carboxaldehyde in place of 4-methylsulfinylbenzaldehyde in Example 2E, the corresponding (Z,E)-5-fluoro-2-methyl-4-(substituted styryl)-indenyl-3-acetic acids are obtained.

EXAMPLE 18

When other acetic acid compounds, obtained in Example 17 above, are used in place of an equivalent amount of 5-fluoro-2-methyl-7-(p-methylsulfinylbenzoyl)-indenyl-3-acetic acid in Example 3 the corresponding amides are formed.

I claim:

1. A method of treating a patient having neoplasia comprising administering a pharmacologically effective amount of a compound of Formula I to the patient with a neoplasia sensitive to such a compound:

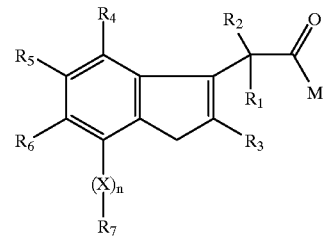

wherein $R_1$ and $R_2$ are independently selected in each instance from the group consisting of hydrogen, alkyl, amino, and —C=O;

$R_3$ is selected from the group consisting of hydrogen and lower alkyl;

M is selected from the group consisting of hydroxy, OMe, or NR' R";

Me is a cation;

R' is selected from the group consisting of hydrogen, loweralkyl, dialkylaminoalkyl, hydroxyalkyl, aminoalkyl, alkoxy, alkenyl, alkynyl, polyhydroxyalkyl, benzyl, phenyl, indane, phenylalkyl, benzylalkyl, pyridinylalkyl, pyrrolylalkyl, pyrrolidinylalkyl, pyrazolylalkyl, pyrazolidinylalkyl, imidazolylalkyl, imidazolidinylalkyl, piperidinylalkyl, pyrazinylalkyl, piperazinylalkyl, pyrimidinylalkyl, morpholinylalkyl, tetrazolylalkyl, triazinylalkyl, furfurylalkyl, thiophenylalkyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl;

R" is selected from the group consisting of hydrogen, lower alkyl, cyanoalkyl, haloalkyl, aminoalkyl, dialkylamino alkyl, alkanoylalkylester and pyridinyl X is selected from the group consisting of lower alkylene, lower alkenylene, lower alkynylene, $S(O)_m$, —C=O, —C(O)O—, —O(O)C—, —S(O)$_2$NR—, —NRS(O)$_2$—, —C(O)NR—, —NRC(O)—, —CH$_2$O, OCH$_2$—, —O—, —NR—, —S(O)$_2$O—, and —OS(O)$_2$—;

R is selected from the group consisting of hydrogen, lower alkyl, and lower alkanoyl;

n is 0 or 1; m is 0,1, or 2;

$R_4$, $R_5$, and $R_6$ are independently selected in each instance from the group consisting of hydrogen, halogen, alkyl, alkanoyloxy, alkoxy, acylamino, alkylamino, dialkylamino, dialkylaminoalkyl, sulfamyl, alkylthio, hydroxy, hydroxyalkyl, alkenyl, alkenyloxy, alkylsulfonyl, alkylsulfinyl, carboxyl, carbalkoxy, carbamido, and cyano;

$R_7$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfryl, and thiophenyl, wherein the substitutents on the $R_7$ ring are one to three substituents selected from the group consisting of halogen, lower alkyl, lower alkoxy, amino, lower alkylamino, hydroxy, nitro, cyano, dilower alkylamino, lower alkyl mercapto, lower alkyl sulfinyl, lower alkyl sulfonyl, acylamino, hydroxyalkyl, carboxyl, carbalkoxy, and carbamido; and pharmaceutically acceptable salts thereof.

2. A method for inhibiting the growth of neoplastic cells comprising exposing the cells to a growth inhibiting effective amount a compound of Formula I:

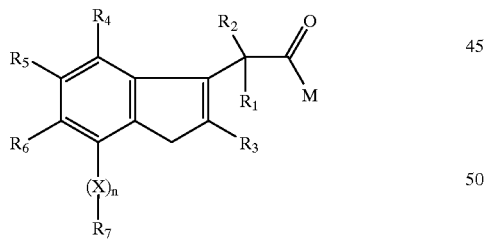

wherein $R_1$ and $R_2$ are independently selected in each instance from the group consisting of hydrogen, alkyl, amino, and —C=O;

$R_3$ is selected from the group consisting of hydrogen and lower alkyl;

M is selected from the group consisting of hydroxy, OMe, or NR' R";

Me is a cation;

R' is selected from the group consisting of hydrogen, loweralkyl, dialkylaminoalkyl, hydroxyalkyl, aminoalkyl, alkoxy, alkenyl, alkynyl, polyhydroxyalkyl, benzyl, phenyl, indane, phenylalkyl, benzylalkyl, pyridinylalkyl, pyrrolylalkyl, pyrrolidinylalkyl, pyrazolylalkyl, pyrazolidinylalkyl, imidazolylalkyl, imidazolidinylalkyl, piperidinylalkyl, pyrazinylalkyl, piperazinylalkyl, pyrimidinylalkyl, morpholinylalkyl, tetrazolylalkyl, triazinylalkyl, furfurylalkyl, thiophenylalkyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl;

R" is selected from the group consisting of hydrogen, lower alkyl, cyanoalkyl, haloalkyl, aminoalkyl, dialkylamino alkyl, alkanoylalkylester and pyridinyl X is selected from the group consisting of lower alkyl, lower alkenyl, lower alkynyl, $S(O)_m$, —C=, —C(O)O—, —O(O)C—, —S(O)$_2$NR—, —NRS(O)$_2$—, —C(O)NR—, —NRC(O)—, —CH$_2$O, OCH$_2$—, —O—, —NR—, —S(O)$_2$O—, and —OS(O)$_2$—;

R is selected from the group consisting of hydrogen, lower alkyl, and lower alkanoyl;

n is 0 or 1; m is 0,1, or 2;

$R_4$, $R_5$, and $R_6$ are independently selected in each instance from the group consisting of hydrogen, halogen, alkyl, alkanoyloxy, alkoxy, acylamino, alkylamino, dialkylamino, dialkylaminoalkyl, sulfamyl, alkylthio, hydroxy, hydroxyalkyl, alkenyl, alkenyloxy, alkylsulfonyl, alkylsulfinyl, carboxyl, carbalkoxy, carbamido, and cyano;

$R_7$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl, and thiophenyl, wherein the substitutents on the $R_7$ ring are one to three substituents selected from the group consisting of halogen, lower alkyl, lower alkoxy, amino, lower alkylamino, hydroxy, nitro, cyano, dilower alkylamino, lower alkyl mercapto, lower alkyl sulfinyl, lower alkyl sulfonyl, acylamino, hydroxyalkyl, carboxyl, carbalkoxy, and carbamido; and pharmaceutically acceptable salts thereof.

3. A method for regulating apoptosis in human cells comprising exposing the cells to an effective amount a compound of Formula I:

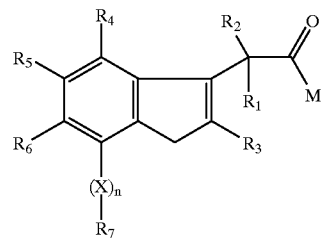

wherein $R_1$ and $R_2$ are independently selected in each instance from the group consisting of hydrogen, alkyl, amino, and —C=O;

$R_3$ is selected from the group consisting of hydrogen and lower alkyl;

M is selected from the group consisting of hydroxy, OMe, or NR' R";

Me is a cation;

R' is selected from the group consisting of hydrogen, loweralkyl, dialkylaminoalkyl, hydroxyalkyl, aminoalkyl, alkoxy, alkenyl, alkynyl, polyhydroxyalkyl, benzyl, phenyl, indane, phenylalkyl, benzylalkyl, pyridinylalkyl, pyrrolylalkyl, pyrrolidinylalkyl, pyrazolylalkyl, pyrazolidinylalkyl, imidazolylalkyl, imidazolidinylalkyl, piperidinylalkyl, pyrazinylalkyl, piperazinylalkyl, pyrimidinylalkyl, morpholinylalkyl, tetrazolylalkyl, triazinylalkyl, furfurylalkyl, thiophenylalkyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl;

R" is selected from the group consisting of hydrogen, lower alkyl, cyanoalkyl, haloalkyl, aminoalkyl, dialkylamino alkyl, alkanoylalkylester and pyridinyl X is selected from the group consisting of lower alkyl, lower alkenyl, lower alkynyl, $S(O)_m$, —C=O, —C(O)O—, —O(O)C—, —$S(O)_2$NR—, —NR$S(O)_2$—, —C(O)NR—, —NRC(O)—, —$CH_2$O, O$CH_2$—, —O—, —NR—, —$S(O)_2$O—, and —O$S(O)_2$O;

R is selected from the group consisting of hydrogen, lower alkyl, and lower alkanoyl;

n is 0 or 1; m is 0,1, or 2;

$R_4$, $R_5$, and $R_6$ are independently selected in each instance from the group consisting of hydrogen, halogen, alkyl, alkanoyloxy, alkoxy, acylamino, alkylamino, dialkylamino, dialkylaminoalkyl, sulfamyl, alkylthio, hydroxy, hydroxyalkyl, alkenyl, alkenyloxy, alkylsulfonyl, alkylsulfinyl, carboxyl, carbalkoxy, carbamido, and cyano;

$R_7$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl, and thiophenyl, wherein the substitutents on the $R_7$ ring are one to three substituents selected from the group consisting of halogen, lower alkyl, lower alkoxy, amino, lower alkylamino, hydroxy, nitro, cyano, dilower alkylamino, lower alkyl mercapto, lower alkyl sulfinyl, lower alkyl sulfonyl, acylamino, hydroxyalkyl, carboxyl, carbalkoxy, and carbamido; and pharmaceutically acceptable salts thereof.

* * * * *